United States Patent [19]

Tran et al.

[11] Patent Number: 5,015,750

[45] Date of Patent: May 14, 1991

[54] PREPARATION OF TRIMETHYLALUMINUM

[75] Inventors: Nam H. Tran, Houston; Dennis L. Deavenport, Seabrook; Curtis W. Post, Friendswood, all of Tex.

[73] Assignee: Texas Alkyls, Inc., Deer Park, Tex.

[21] Appl. No.: 606,669

[22] Filed: Oct. 31, 1990

[51] Int. Cl.$^5$ .............................................. C07F 5/06
[52] U.S. Cl. .................................... 556/187; 556/170
[58] Field of Search ................................. 556/187, 170

[56] References Cited

U.S. PATENT DOCUMENTS

| | | | |
|---|---|---|---|
| 2,786,860 | 3/1957 | Ziegler et al. | 556/170 |
| 2,839,556 | 6/1958 | Ziegler et al. | 556/187 |
| 2,863,894 | 12/1958 | Smith | 556/187 |
| 2,909,547 | 10/1959 | Ziegler et al. | 556/187 |
| 3,006,942 | 10/1961 | Nobis | 556/187 |

FOREIGN PATENT DOCUMENTS

| | | | |
|---|---|---|---|
| 0772174 | 4/1957 | United Kingdom | 556/170 |
| 0779873 | 7/1957 | United Kingdom | 556/187 |

OTHER PUBLICATIONS

Lyle F. Albright, "The Properties, Chemistry and Synthesis of Alkyl Aluminums," Chemical Engineering, Dec. 4, 1967, pp. 179–186.

*Primary Examiner*—Arthur C. Prescott
*Assistant Examiner*—Porfirio Nazario-Gonzalez
*Attorney, Agent, or Firm*—Richard P. Fennelly; Louis A. Morris

[57] ABSTRACT

Trimethylaluminum can be formed by reacting a methylaluminum chloride, such as dimethylaluminum chloride, with sodium in the presence of an effective amount of an alkali or alkaline earth metal fluoride (e.g., sodium fluoride) to enhance the reaction.

8 Claims, No Drawings

PREPARATION OF TRIMETHYLALUMINUM

BACKGROUND OF THE INVENTION

Trimethylaluminum (TMAL) has the potential of becoming a significant commercial product with many applications such as a polymerization co-catalyst, a substrate for production of compound semiconductors, a starting material to produce trimethylgallium and methylaluminoxanes, and so forth.

Several methods have been known for trimethylaluminum synthesis such as the "Magalium" process (U.S. Pat. No. 2,744,127), the cryolite process (U.S. Pat. No. 2,839,556), the phenyl sodium process (Adv. Inorg. Chem. Radiochem. 7, 269, 1967), the Grignard route (K. Ziegler, Organometallic Chemistry (ACS Monograph No. 147) p. 197, 1960), and so forth. The alkali reduction method has been the process most extensively used in the industrial as well as the laboratory scale preparation.

The overall reaction is described by Grosse and Mavity, J. Org. Chem., Vol. 5, pp. 106-121 as follows:

$$3\ Me_2AlCl + 3\ Na° \rightarrow 2\ Me_3Al + Al° + 3\ NaCl$$

This method involves reacting dimethylaluminum chloride (DMAC) with molten metallic sodium which is dispersed in a suitable hydrocarbon solvent. TMAL produced can be isolated by vacuum distillation. The yield obtained by this method is low because the resulting sodium chloride and metallic aluminum deposit a coating on the surface of sodium metal. This effect which can cause severe reaction fouling may be magnified by the side reaction between TMAL and excess sodium to produce metallic aluminum and insoluble sodium tetramethylaluminate.

$$4\ Me_3Al + 3\ Na° \rightarrow 3\ Me_4AlNa + Al°$$

The sodium reduction of DMAC has been studied in glassware using several different solvents (Soltrol 160 solvent, Tetralin solvent, n-heptane, n-decane, and dodecane). The yields ranged from 47% to 85% and the product was contaminated with unreacted DMAC even though excess sodium was used.

Experimental work has also been conducted earlier whereby DMAC was reacted with sodium as the sole reducing agent in a larger, pilot plant reactor. Although a yield of about 70% was obtained, a large excess of sodium and a very long reaction time was required for complete reduction of DMAC. In addition, reactor fouling due to formation of by-products was severe.

From these experiments, it can be concluded that there are numerous drawbacks to this route: The yield is low; sodium chloride and metallic aluminum by-products and unreacted sodium form a considerable amount of lumps which are difficult or impossible to transfer out of reactor causing problems in waste disposal and safety; the reduction does not readily go to completion resulting in a product which is contaminated with unreacted DMAC and; excess sodium is required for a complete reduction to take place at a reasonable rate. A larger excess of sodium is undesirable due to yield loss (reaction 2) and reactor fouling. This side reaction reduces the amount of TMAL produced and thus diminishes the final yield; reaction time is long; and the use of high boiling solvents gives reduced yield and purity (unreacted DMAC contamination in distilled product). But high boiling solvents are desirable because they remain in the vessel after TMAL recovery to fluidize the solid by-products, NaCl and Al°. In contrast, lower boiling point solvents codistill with TMAL to contaminate final product.

SUMMARY OF THE INVENTION

The instant invention relates to an improved process for the synthesis of trimethylaluminum (TMAL) from such methylaluminum chlorides as dimethylaluminum chloride (DMAC) using sodium with an effective amount of an alkali or alkaline earth metal to enhance the conversion to TMAL. The methylaluminum chloride starting material can be dimethylaluminum chloride, methylaluminum dichloride, or methylaluminum sesquichloride. The fluoride which is used in the process is believed to act as a catalyst to first convert the methylaluminum chloride to the corresponding fluoride which is then more easily reduced by the sodium with the regeneration of the fluoride during the reaction between the fluoride and the sodium, thus allowing further exchange with the unreacted methylaluminum chloride. However, the present inventors do not wish to be bound by this theory since it is clear that the fluoride is effective for the intended reaction despite whatever particular mechanism or reaction pathway is, in actuality, responsible.

DETAILED DESCRIPTION OF THE INVENTION

In accordance with a preferred embodiment of the instant process in which dimethylaluminum chloride is the selected methylaluminum chloride used, the Grosse-Mavity method of using sodium to reduce dimethylaluminum chloride to trimethylaluminum is improved by the use of n alkali or alkaline earth metal fluoride to enhance the conversion of the chloride starting material to the desired trimethylaluminum product. Examples of suitable fluorides to use are sodium fluoride, potassium fluoride, and calcium fluoride.

In a preferred embodiment of the instant process, DMAC and sodium are added stepwise in stoichiometric quantity to a flask containing a small amount (e.g., from about 1 mole % to about 10 mole % by weight of the two previous reactants) of an alkali metal fluoride, which is preferably sodium fluoride, in a high boiling solvent, such as mineral oil. The contents are heated and maintained at 120°-140° C. during charging of reactants. After the addition is completed, the reaction mixture is maintained at 140° C. together with stirring for an additional period of time (e.g., four hours) to allow for substantial completion of the reaction. Trimethylaluminum is then isolated by 1-plate vacuum distillation.

In its simplest form, the new process (in a preferred embodiment) is thought to involve converting DMAC to DMAF by sodium fluoride; then sodium is added to reduce DMAF to TMAL, and the sodium fluoride charged in the reaction flask is regenerated. The reaction steps are repeated. The probable reaction scheme is illustrated below, although applicants do not wish to be bound by this theory:

$$3\ Me_2AlCl + 3\ NaF \rightarrow 3\ Me_2AlF + 3\ NaCl$$

$$3\ Me_2AlF + 3\ Na° \rightarrow 2\ Me_3Al + Al° + 3\ NaF$$

Several advantages of the subject process (in its preferred embodiment) and the resulting TMAL are: The yield is significantly improved (approximately 90%); no efficient multiple plate distillation column is required for separating TMAL from reaction mixture because mineral oil stays behind in the flask after TMAL recovery; the by-product solids are finely dispersed in mineral oil and easily removed from the reaction flask; solvent amount used in this process is considerably less than shown in previous work; and an excess of sodium is not needed to achieve high conversion, consequently, it is unnecessary to deactivate unreacted sodium and sodium tetramethylaluminate from the reaction waste following TMAL recovery; reaction times are greatly reduced; and the TMAL collected normally contained less than 0.03 wt % Cl.

The present invention is further illustrated by the Examples which follow.

EXAMPLES 1-2

The apparatus used in this Example as well as those which follow comprised a four-necked 2-liter flask equipped with a mechanical agitator, thermowell, dropping funnel, sodium bead charge port, and an oil jacketed condenser provided with a stillhead and a receiver. The flask was heated in an oil bath.

Sodium fluoride (4.2 gm, 0.1 mole) and mineral oil (200 ml) were added to the reaction flask. The slurry was heated and maintained at 140° C. at a pressure of 10 torr to remove any low boiling point compounds and air. Dimethylaluminum chloride (DMAC) (185.0 gm, 2.00 moles) from the dropping funnel and sodium beads (43.9 gm, 1.98 moles) were added stepwise in increments of approximately 0.1 mole each to the flask. The time allowed for each increment of DMAC and sodium addition averaged 15 minutes. The reaction mixture was heated and maintained at 120°-140° C. during the time the reactants were added. After completing the additions, stirring was continued together with heating for an additional four hours. Trimethylaluminum (TMAL) was isolated from the reaction mixture via 1-plate vacuum distillation. A total of 88 gm of chloride-free TMAL (assay=95.4 wt %) was collected. The yield was 89.2% of theoretical.

In a second Example the conditions and quantity of starting materials were kept approximately the same as those in Example 1 except that distilled DMAC was used. Crude TMAL collected overhead was 97.98 wt % purity with <0.03 wt % DMAC and no hydride. This represented an 86.5% yield relative to theory.

The bottoms of the reactors from Examples 1 and 2 were black, slightly viscous, free-flowing and non-pyrophoric. The bottoms waste was transferred smoothly through a ¼ inch tubing of TEFLON fluorocarbon polymer using 5 psig nitrogen pressure. No lumps or unreacted sodium beads were observed in the bottoms.

EXAMPLE 3

Sodium fluoride (5.5 gm, 0.138 mole) and DMAC (188 gm, 2.032 moles) were added in the reaction flask containing 138 gm ISOPAR-H solvent. The mixture was heated to 127° C. Sodium beads (46.3 gm, 2.011 moles) were then added slowly for a total of 70 minutes. The flask temperature was maintained at 127°-143° C. during the reaction. After completing the addition, the reaction mixture was heated at 136°-150° C. together with stirring for an additional five hours. The flask was then allowed to cool and settle overnight. TMAL was distilled out of the reaction mixture the next morning. A considerable amount of lumps formed during the reaction period caused problems during waste transfer. Analysis of the distillate (145.4 gm) showed 23.86 wt % Al and 1.24 wt % Cl. This indicated 61.21 wt % TMAL, 3.25 wt % DMAC with the difference being solvent. The yield was 91.1% of theoretical.

EXAMPLE 4

Sodium beads (45.8 gm, 1.991 moles) were added to a reaction flask containing mineral oil (200 ml). The flask and its contents were heated to a temperature of 135°-150° C. The contents were stirred vigorously to allow molten sodium to be well dispersed in mineral oil. Then DMAC from the dropping funnel was added dropwise. After all the DMAC (about 85 minutes) had been added, stirring was continued with heating for an additional two and one-half hours. The reaction mixture was allowed to cool to room temperature. Sodium fluoride (3.5 gm, 0.833 mole) was added to the reaction flask. The next morning, the contents were stirred, heated to 138° C. and maintained at this condition for several hours. TMAL then was isolated by 1-plate vacuum distillation. The reactor fouling was moderately severe. Analysis of the distillate (87.9 gm) showed 35.45 wt % Al and 0.14 wt % Cl. This represented 94.64 wt % TMAL, 0.31 wt % DMAC with the difference being diluents. The yield was calculated as 89.6% of theoretical.

EXAMPLE 5

This Example demonstrates successful scale-up of the reaction in a ten gallon reactor.

Crude DMAC (8000 gm) and sodium (2000 gm, 86.96 moles) were added stepwise (4.35 moles of each reactant for each increment) to a ten gallon reactor containing sodium fluoride (185 gm, 4.36 moles) in mineral oil (8000 gm). The reactor contents were heated and were maintained at 135°-148° C. under a pressure of 10 psig during charging of the reactants. After completion of the additions, the reaction mixture was heated and was stirred for another hour at 150° C. Crude TMAL was then separated from the reactor mixture via vacuum flask distillation. A total of 3987 gm of distillate was collected overhead. Analysis indicated that the final product contained 93.95 wt % TMAL, 1.23 wt % TEAL, 0.33 wt % DMAC and the difference (4.42 wt %) being diluents related to impurities in the crude starting DMAC. The yield was 93.2% of theoretical.

The resulting reactor bottoms were removed easily through a ½ inch outer diameter dip tub via a ⅜ inch tubing of TEFLON fluoropolymer tubing to a slop cylinder. According to a materials balance calculation, 97.9% of the bottoms were removed with only about 600 gm left in the reactor. The bottoms were black, slightly viscous, free-flowing and non-pyrophoric. No lumps were observed in the bottoms. The reactor residue was washed out with four gallons of toluene.

EXAMPLE 6

The conditions and quantity of starting materials were kept approximately the same as those in Example 1 except that potassium fluoride (KF) was used as a catalyst instead of NaF.

DMAC with 96.1% purity (171.4 gm, 1.78 moles) and sodium (42.1 gm, 1.81 moles) were added stepwise in 0.1 mole increments to a reaction flask containing potassium fluoride (6.0 gm, 0.103 mole) in mineral oil (250 gm). The flask temperature was maintained at 135°-150° C. during charging of the reactants. After the first addition cycle, after 10 cc of DMAC had been added, gummy white solids were formed. The first increment of sodium was then added. Digestion of the sodium beads was not observed indicating that the KF formed a complex with DMAC and this complex could not be reduced by sodium. Addition of the reactants was continued. The reaction appeared to take place when the third cycle of DMAC was added. After completion of reactant addition, the reaction mixture was heated for another hour at 150° C. TMAL was then separated from the mixture via 1-plate vacuum distillation. A total of 69.6 gm of distillate was collected. Analysis showed that the distillate contained 93.7 wt % TMAL, 0.11 wt % TEAL, no chloride and a trace of hydride. The resulting bottoms of the reaction flask were black and slightly viscous, and contained some granular lumps and unreacted sodium. The yield was 76.3% of theory.

EXAMPLE 7

Preparation of TMAL via sodium reduction of DMAC using calcium fluoride (instead of sodium fluoride) as a catalyst was conducted in small-scale glassware which is described in Example 1.

DMAC with 96.1% purity (181.5 gm, 1.885 moles) and sodium (43.4 gm, 1.885 moles) were added stepwise in 0.1 mole increments to a reaction flask containing calcium fluoride (3.95 gm, 0.0506 mole) in mineral oil (250 gm). The flask temperature was maintained at 130°-160° C. during charging of the reactants. After completion of reactant addition, the reaction mixture was heated for another hour at 140° C. TMAL was then separated from the mixture via 1-plate vacuum distillation. A total of 92.2 gm of distillate was collected. The analysis showed the distillate contained 85.0 wt % TMAL, 0.1 wt % TEAL, 9.8 wt % DMAC, and no hydride. The resulting bottoms left in the reaction flask were black and viscous. Due to the thickness of the slurry, the bottoms could not be transferred out of the flask through a ⅜ inch tube of TEFLON fluoropolymer with 5 psig nitrogen pressure although no lumps or large particles were observed in the slurry. The yield was calculated at 86.6% of theory.

COMPARATIVE EXAMPLE 8

In this Example, no catalyst was used in the reaction. The conditions and quantity of starting materials were kept approximately the same as those in Example 1.

DMAC with 96.1% purity (179.5 gm, 1.864 moles) and sodium (44.65 gm, 1.941 moles) were added stepwise in 0.1 mole increments to a reaction flask containing mineral oil (250 gm). The reaction temperature was maintained at 130°-150° C. during charging of the reactants. After the addition, the reactor mixture was kept at 150° C. for another hour. TMAL was then removed from the reaction mixture by vacuum distillation. A total of 96.2 gm of distillate was collected. It was found that the distillate contained 67.97 wt % TMAL, 0.14 wt % TEAL, 28.85 wt % DMAC, a trace of hydride, and the difference being diluents. The resulting bottoms could not be transferred out of the flask via ⅜ inch TEFLON brand tubing using a pressure of 5 psig nitrogen. The bottoms slurry contained a considerable amount of lumps and unreacted sodium. The yield was 73.1% of theory.

EXAMPLE 9

In this Example, TMAL was prepared by reacting methylaluminum sesquichloride (MASC) with sodium metal in the presence of a catalytic amount of NaF.

MASC (171.7 gm, 0.836 mole) and sodium (58.0 mg, 2.522 moles) were added stepwise in increments of 0.056 mole of MASC and 0.17 mole of sodium into a flask containing sodium fluoride (7.1 mg, 0.17 mole) and TMAL (7.0 gm, 0.0971 mole) in mineral oil (350 gm). The flask temperature was maintained at 135°-154° C. during charging of the reactants. After completion of reactant addition, the reaction mixture was heated for another hour at 150° C. TMAL was then separated from the mixture via 1-plate vacuum distillation. A total of 63.6 gm of distillate was collected. The analysis indicated that the distillate contained 85.6 wt % TMAL, 8.1 wt % DMAC, 0.2 wt % TEAL, and no hydride. The resulting bottoms of the reaction flask were black and quite viscous, as well as containing a substantial amount of granular lumps and unreacted sodium. The yield was 78.9% of theory.

The foregoing Examples are illustrative of certain embodiments of the present invention and, for that reason, should not be construed in a limiting sense. The scope of protection sought is set forth in the claims which follow.

We claim:

1. In a process for the production of trimethylaluminum from a methylaluminum chloride by sodium reduction, wherein the improvement comprises use of an effective amount of an alkali or alkaline earth metal fluoride to convert the methylaluminum chloride to trimethylaluminum.

2. A process as claimed in claim 1 wherein the alkali metal fluoride is sodium fluoride.

3. A process as claimed in claim 1 the methylaluminum chloride is dimethylaluminum chloride.

4. A process as claimed in claim 2 the methylaluminum chloride is dimethylaluminum chloride.

5. A process as claimed in claim 1 the methylaluminum chloride is methylaluminum sesquichloride.

6. A process as claimed in claim 2 the methylaluminum chloride is methylaluminum sesquichloride.

7. A process as claimed in claim 1 wherein the amount of fluoride ranges from about 1 mole % to about 10 mole % by weight of the sodium and methylaluminum chloride.

8. A process as claimed in claim 4 wherein the amount of fluoride ranges from about 1 mole % to about 10 mole % by weight of the sodium and methylaluminum chloride.

* * * * *